(12) United States Patent
Bruck et al.

(10) Patent No.: US 11,703,463 B2
(45) Date of Patent: *Jul. 18, 2023

(54) NON-DESTRUCTIVE ASSESSMENT OF CORN ROOTWORM DAMAGE

(71) Applicant: PIONEER HI-BRED INTERNATIONAL, INC., Johnston, IA (US)

(72) Inventors: Denny Joseph Bruck, Johnston, IA (US); Kaley J Gade, Des Moines, IA (US); Albert L Lu, West Des Moines, IA (US); Timothy Michael Moriarty, Urbandale, IA (US); Angel O Ortiz Lozada, Des Moines, IA (US); Gary A Sandahl, West Des Moines, IA (US); Gerardus W A M Van Der Heijden, Grimes, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/659,753

(22) Filed: Apr. 19, 2022

(65) Prior Publication Data

US 2022/0307993 A1    Sep. 29, 2022

Related U.S. Application Data

(63) Continuation of application No. 16/893,148, filed on Jun. 4, 2020, now Pat. No. 11,333,618.

(Continued)

(51) Int. Cl.
G06T 7/00 (2017.01)
G06T 7/62 (2017.01)
(Continued)

(52) U.S. Cl.
CPC ......... *G01N 23/046* (2013.01); *G01N 23/083* (2013.01); *G01N 23/18* (2013.01);
(Continued)

(58) Field of Classification Search
CPC .... G01N 23/046; G01N 23/083; G01N 23/18; G01N 33/0098; G01N 2223/04;
(Continued)

(56) References Cited

U.S. PATENT DOCUMENTS 8,341,880 B2    1/2013  Lejeune et al.
11,333,618 B1 *  5/2022  Bruck ................... G06T 7/0012
(Continued)

FOREIGN PATENT DOCUMENTS

EP    2936435 B1    6/2019

OTHER PUBLICATIONS

Oleson et al. 2005, Journal of Economic Entomology 98:1, p. 1-8.
(Continued)

*Primary Examiner* — Mark R Gaworecki (57) ABSTRACT

The present embodiments generally relate to methods of non-destructively imaging plant root damage by insect root herbivores and evaluating the efficacy of insecticidal materials associated with the roots of plants against the insect root herbivores, useful for automated high throughput bioassays.

23 Claims, 5 Drawing Sheets

Related U.S. Application Data (60) Provisional application No. 62/858,660, filed on Jun. 7, 2019.

(51) Int. Cl.
  *G01N 23/04* (2018.01)
  *G01N 23/083* (2018.01)
  *G01N 33/00* (2006.01)
  *G01N 23/18* (2018.01)
  *G01N 23/046* (2018.01)

(52) U.S. Cl.
  CPC ....... *G01N 33/0098* (2013.01); *G06T 7/0012* (2013.01); *G06T 7/62* (2017.01); *G01N 2223/04* (2013.01); *G01N 2223/30* (2013.01); *G01N 2223/401* (2013.01); *G01N 2223/419* (2013.01); *G01N 2223/646* (2013.01); *G06T 2207/10081* (2013.01); *G06T 2207/10116* (2013.01)

(58) Field of Classification Search
  CPC ......... G01N 2223/30; G01N 2223/401; G01N 2223/419; G01N 2223/646; G06T 7/0012; G06T 7/62; G06T 2207/10081; G06T 2207/10116
  See application file for complete search history.

(56) References Cited

U.S. PATENT DOCUMENTS

| | | |
|---|---|---|
| 2016/0025697 A1 | 1/2016 | Alt |
| 2018/0348186 A1 | 12/2018 | Benfey |
| 2019/0195762 A1 | 6/2019 | Brune |

OTHER PUBLICATIONS

Metzner, R., et al., Direct comparison or MRI and X-ray CT technologies for 3D imaging of root systems in soil potential and challenges for root trait quantification, Plant Methods, 11:17 (2015).

Douarre, C., et al., Transfer Learning from Synthetic Data Applied to Soil-Root Segmentation in X-ray Tomography Images, J. Imaging, 4(5):65 (2018).

* cited by examiner

NON-DESTRUCTIVE ASSESSMENT OF CORN ROOTWORM DAMAGE

CROSS-REFERENCE TO RELATED APPLICATIONS

This application claims the benefit of U.S. Provisional Application No. 62/858,660, filed Jun. 7, 2019, which is hereby incorporated herein in its entirety by reference.

FIELD

The present embodiments generally relate to methods of non-destructively imaging plant root damage by insect root herbivores and evaluating the efficacy of insecticidal materials associated with the roots of plants against the insect root herbivores, useful for automated high throughput bioassays. The present embodiments also relate to comparing root volume, root length, root growth rate, root branching morphology, or root depth distribution of plants to access phytotoxicity of a trait.

BACKGROUND

Corn rootworm (*Diabrotica* spp.) can cause considerable damage to maize plants. Before corn-rootworm-resistant biotech traits were available on the market, annual yield losses and control costs for western corn rootworm (*D. virgifera virgifera*) and northern corn rootworm (*D. barber*) were estimated to exceed $1 billion in 2002 (Mitchell, Gray, & Steffey, 2002). The primary approach to controlling corn rootworm involves using transgenic insect control traits and application of insecticides. The potential exists for rootworm populations to develop resistance to *Bacillus thuringiensis* traits. Therefore, there remains a need to identify and develop new traits to provide adequate plant root protection against insect root herbivores.

The effect of proteins on rootworms may be assessed by transforming plants with potential resistance genes and infesting the soil of these plants with rootworm. After some incubation time, the root system damage of a plant extracted from the soil may be visually assessed, by manually assigning a plant a so-called Root Nodal Injury Score (See e.g. Oleson, J D, et al., J Econ Entomol., 98(1):1-8 (2005)). Similar methods for manual scoring are also used for assessment of the efficacy of non-transgenic methods of control related to materials such as seed treatments.

Manual assessment and scoring may involve a considerable amount of handwork and human interpretation/training, as well as direct plant manipulation that may cause damage to a plant by, for example, pulling roots and/or washing roots. A non-destructive assessment method amenable to automation is desirable for increasing throughput and improving overall plant vigor, agronomics and seed set.

BRIEF SUMMARY

Methods are provided for non-destructively assessing damage to plant roots from insect root herbivores. In one embodiment, methods are provided for non-destructively determining the resistance of plant roots to insect herbivory, comprising subjecting root tissue of a candidate plant comprising at least one insecticidal material associated with said root tissue to at least one insect root herbivore, obtaining a non-destructive image of roots of said candidate plant, and generating a root nodal injury score.

In another embodiment is provided a method of non-destructively assaying the efficacy of an insecticidal material to prevent insect root herbivory, comprising subjecting root tissue of a candidate plant comprising at least one insecticidal material associated with said root tissue to at least one insect root herbivore, presenting the candidate plant to a non-destructive imaging apparatus and obtaining a non-destructive image of roots of said candidate plant. A root nodal injury score may then be determined based on the non-destructively obtained image.

The methods disclosed herein contemplate that the steps may be conducted manually, the steps may be automated, or some combination thereof. Methods are provided for assaying the activity of insecticidal materials using an automated system. In some embodiments, methods are provided relating to assaying the activity of insecticidal compounds using an automated system comprising providing a candidate plant with at least one insect root herbivore; transporting the candidate plant to an imaging apparatus for imaging of the roots of the candidate plant; generating a non-destructive image of roots of the candidate plant, and generating a root nodal injury score.

In one embodiment, the candidate plant is presented to the non-destructive imaging apparatus using an automated movement system, such as for example, a transportation or conveyor belt. The methods disclosed herein may be used in a high-throughput manner to evaluate the root systems of numerous candidate plants. In one embodiment, the methods have at least two non-destructive imaging apparatuses, each with an automated movement system, capable of imaging the root systems of multiple candidate plants sequentially or simultaneously.

The non-destructive imaging apparatus may comprise an X-ray imager or magnetic resonance imager (MM). The non-destructive image may be generated by X-ray computed tomography (CT).

In one embodiment, the insect root herbivore is a Coleopteran insect, such as a member of the *Diabrotica* species, for example *Diabrotica virgifera* LeConte (western corn rootworm); *D. barberi* Smith and Lawrence (northern corn rootworm); or *D. undecimpunctata howardi* Barber (southern corn rootworm). In another embodiment, the insecticidal material comprises an insecticidal protein expressed in or applied to root tissue of a candidate plant; a double-stranded RNA generated in or applied to root tissue of a candidate plant; a biological insecticide, for example insecticidal microbes or nematodes; or a chemical insecticide applied to the root tissue of a candidate plant.

DETAILED DESCRIPTION

The embodiments of the invention are not limited by the exemplary methods and materials disclosed, and any methods and materials similar or equivalent to those described can be used in the practice or testing of embodiments of this invention. Numeric ranges are inclusive of the numbers defining the range.

The articles "a" and "an" are used to refer to one or more than one (i.e., to at least one) of the grammatical object of the article. For example, "an element" means one or more elements.

As used herein, "IC-50" or inhibition concentration, and "EC-50" or effective concentration each may be used interchangeably, and refers to the concentration at which the larvae size (as may be determined by the larvae pixel area) is half way between the maximum size (the zero dose control), and the smallest size (the most toxic dose). (See Ritz (2010) Environmental Toxicology and Chemistry 29:220-229, Ali and Luttrell (2009) Journal of Economic Entomology 102:1935-1947, Brvault et al. (2009), Journal of Economic Entomology 102:2301-2309, Kerr and Meador (1996), Environmental Toxicology and Chemistry 15:395-401, Marcon et al (1999) Journal of Economic Entomology 92:279-229).

In one embodiment of the invention, a method is provided for non-destructively determining the resistance of plant roots to insect herbivory, comprising subjecting root tissue of a candidate plant comprising at least one insecticidal material associated with said root tissue to at least one insect root herbivore, obtaining a non-destructive image of roots of said candidate plant, and generating a root nodal injury score or other determination of the effects of the insecticidal material associated with said root tissue. In one embodiment, the candidate plant is presented to the imaging apparatus by an automated movement system, such as for example a conveyor belt system.

In another embodiment, a method is provided for non-destructively assaying the efficacy of an insecticidal material to insect root herbivory, comprising subjecting root tissue of a candidate plant comprising at least one insecticidal material associated with said root tissue to at least one insect root herbivore, presenting the candidate plant to a non-destructive imaging apparatus, obtaining a non-destructive image of roots of said candidate plant, and generating a root nodal injury score or other determination of the effects of the insecticidal material associated with said root tissue. In one embodiment, the candidate plant is presented to the imaging apparatus by an automated movement system, such as for example a conveyor belt system.

Methods are provided for assaying the activity of insecticidal materials using an automated system. In an embodiment, methods are provided relating to assaying the activity of insecticidal materials using an automated system comprising providing at least one candidate plant in a container; transporting by automated means said container to an imaging device for imaging of the roots of the candidate plant; and obtaining an image of the roots of the candidate plant for measuring or determining a corn rootworm nodal injury score or other determination of the effects of the insecticidal material associated with said root tissue.

In another embodiment, the method further includes the step of infesting insects or insect eggs into a plant container comprising a candidate plant. In another embodiment, the method relates to infesting more than one insect or insect egg per plant. In one embodiment, the method relates to infesting a predetermined number of insects or insect eggs equally into a plurality of candidate plants.

In a further embodiment, a candidate plant contains an insecticidal material. In one embodiment the insecticidal material comprises at least one of the group consisting of an insecticidal protein, an insecticidal silencing element or double stranded RNA, a biological insecticide, for example insecticidal microbes or nematodes; or an insecticidal chemistry, or combinations thereof.

In one embodiment, the plant container may comprise an identifying code, such as for example a barcode or an RFID chip. In this embodiment, it is contemplated that the automated system can further comprise at least one barcode or RFID chip reader as is known in the art, which can be communicatively coupled to a computer or other processing equipment as further disclosed herein. In one embodiment the plant container is a white, clear, opaque, or other colored plant container.

In another embodiment, a method is provided for non-destructively determining the resistance of plant roots to insect root herbivores. In one embodiment, the method of non-destructively determining the resistance of plant roots to insect root herbivory comprises subjecting root tissue of a candidate plant comprising at least one insecticidal material associated with said root tissue to at least one insect root herbivore, obtaining a non-destructive image of roots of said candidate plant, and generating a root nodal injury score or other determination of the effects of the insecticidal material associated with said root tissue. The non-destructive image may be obtained using an imaging system comprising x-ray equipment or magnetic resonance imaging (MM) equipment configured to produce images and identify shapes, patterns, orientation, and or other characteristics of objects. In one embodiment, the measurement comprises detecting and/or recording root patterns of a candidate plant in a plant container.

In a further embodiment, the detecting and/or recording of the root patterns of a candidate plant comprises comparing two or more images from a time interval of a candidate plant in a plant container. In this embodiment, the two or more images can be compared using imaging software stored on an imaging computer as further disclosed herein. For example, such imaging software can be configured to produce an output corresponding to a visual overlay of discrete images, taken at various times during the time interval, with such output being presented on a display device positioned in communication with a processor of the imaging computer. In use, it is contemplated that the displayed output can create a reference value that can be used to measure changes in root patterns, root mass (or area), or root nodes in the presence of insect root herbivores over time. In another embodiment, the measurement comprises a metric measurement. In this embodiment, it is contemplated that the metric measurement can be determined using imaging software stored on a computer as further disclosed herein, with the imaging software being configured to determine the size, length, or volume of roots of a candidate plant or a portion thereof by processing a previously captured image of the roots of a candidate plant or a portion thereof.

In one embodiment, the CT scan image is obtained from a soil medium comprising about 38% peat, about 51% Bark, about 8% Perlite, and about 3% Vermiculite. In another embodiment, the image is obtained from a soil medium comprising about 77% Peat, about 16% Perlite, and about 7% Vermiculite. In another embodiment, the moisture content of the soil medium at the time of CT scan imaging ranges from about 10% to about 40%. In another embodiment, the candidate plant is subjected to evaluation using an MM-based system.

In one embodiment, the method relates to determining the efficacy or insecticidal activity of an insecticidal material associated with roots of a candidate plant, such as an insecticidal protein, an insecticidal silencing element or double stranded RNA, a non-protein insecticidal chemical, a native trait or characteristic of a plant that confers resistance or tolerance to insect herbivory. In one embodiment, the test substance is a new insecticidal protein, a shuffled variant, or a domain swapped insecticidal protein. In another embodiment, the insecticidal protein is an unknown protein or a protein of unknown toxicity or insecticidal activity to insects. In a further embodiment, the assay comprises the use of a positive control test plant comprising an insecticidal protein, wherein the toxicity of the positive control insecticidal protein is known. In one embodiment, the toxicity of a test protein is determined by determining an IC-50, EC-50 or an LC-50 of the test protein.

In one embodiment, the method relates to determining the effect of an insecticidal protein, an insecticidal silencing element or double stranded RNA, or a non-protein insecticidal chemical, trait or insecticide, on root development. In another embodiment, the method relates to determining the effect of a native trait or characteristic of a plant on root development.

Roots of transgenic plants expressing pesticidal proteins may be evaluated for resistance to herbivory against one or more insect pests. In a preferred embodiment, the pesticidal protein has activity against below-ground insect pests. In one embodiment, the pesticidal proteins are selected from, but are not limited to: insecticidal proteins such as; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD084 polypeptide, an IPD085 polypeptide, an IPD086 polypeptide, and an IPD089 polypeptide of PCT Publication Number WO2018084936A1; PIP-72 polypeptide of US Patent Publication Number US20160366891; an IPD098 polypeptide and an IPD109 polypeptide of PCT Publication Number WO 2018/232072; an IPD079 polypeptide of PCT Publication Number WO2017/23486; an IPD082 polypeptide of PCT Publication Number WO 2017/105987, an IPD090 polypeptide of PCT Publication Number WO 2017/192560, an IPD093 polypeptide of PCT Publication Number WO 2018/111551; an IPD101 polypeptide of PCT Publication Number WO 2018/118811, and δ-endotoxins including, but not limited to, the Cry1, Cry3, Cry6, Cry7, Cry8, Cry14, Cry18, Cry22, Cry23, Cry26, Cry 28, Cry34, Cry35, Cry36, Cry37, Cry38, Cry43, Cry45, Cry55, and Cry75 classes of δ-endotoxin genes and the *B. thuringiensis* cytolytic Cyt1 and Cyt2 genes.

In one embodiment, an automated root imaging system can comprise at least one automated movement system as further disclosed herein. The automated movement system can have its own processing circuitry, which can be configured to control operation of the automated movement system and other system components as disclosed herein. Optionally, the processing circuitry of the automated movement system can comprise a central control (master) computer. Plants may be transported to and from the scanner manually, or via an automated handling/logistics system incorporated into the growing environment that is in operative communication with the X-ray scanner.

In another embodiment, the imaging system can further comprise at least one imaging assembly. In this embodiment, the imaging assembly can comprise a camera, an X-ray or MM system, and one or more sensors. The imaging apparatus can comprise a stage configured to receive and support a pot comprising a candidate plant while a camera, X-ray or MRI system captures images of one or more candidate plants. In one embodiment, the image is generated using a helical scan, in which the imaging sensor rotates around a candidate plant that is held in a stationary position. In another embodiment, the image is generated using a stationary imaging sensor while a candidate plant is rotated before the imaging sensor.

The imaging apparatus can be communicatively coupled to processing circuitry, which can permit selective control of the operation (e.g., activation and image acquisition parameters) of the imaging apparatus. In use, the processing circuitry of the imaging apparatus can be communicatively coupled (e.g., integrally connected or wirelessly connected) to processing circuitry of an automated movement system using conventional mechanisms.

Multiple automated imaging systems operating simultaneously or sequentially are contemplated herein. Each imaging system can have its own processing circuitry (e.g., a computer) that is configured to permit selective control of the operation of the imaging system. In use, the processing circuitry of each imaging system can be communicatively coupled (e.g., integrally connected or wirelessly connected) to processing circuitry of an automated movement system using conventional mechanisms, such as ActiveX control and/or serial port connection.

In a further embodiment, the automated imaging system can comprise at least one bar code or RFID chip reader positioned at selected locations within the system to permit tracking of the locations of individual candidate plants. Each bar code reader can comprise processing circuitry that is configured to transmit information concerning the detection and scanning of bar codes (e.g., time, location, plant identification and the like). Optionally, each bar code reader can be communicatively coupled to an automated movement system. Additionally, or alternatively, each bar code reader can be communicatively coupled to a master computer or remote computing device.

In the description of imaging operations provided herein, it is contemplated that all steps of the imaging process can be performed in an automated manner. Where specific structure for performing a step is not provided in the description, it is understood that such step can be performed by corresponding processing circuitry as disclosed herein, which can control operation of system components or conduct analysis in an automated manner.

Image segmentation algorithms have been developed that are useful for identifying roots of candidate plants in pots comprising soil. See Metzner, R., et al., Direct comparison or MRI and X-ray CT technologies for 3D imaging of root systems in soil: potential and challenges for root trait quantification, Plant Methods, 11:17 (2015); Douarre, C., et al., Transfer Learning from Synthetic Data Applied to Soil-Root Segmentation in X-ray Tomography Images, J. Imaging, 4(5):65 (2018).

In alternative embodiments, the methods and systems disclosed herein, in whole or in part, may implement a machine, computer system or equivalent, within which a set of instructions for causing the computer or machine to perform any one or more of the protocols or methodologies of the invention may be executed. In alternative embodiments, the machine may be connected (e.g., networked) to other machines, e.g., in a Local Area Network (LAN), an intranet, an extranet, the Internet, or in cloud computing, or any equivalents thereof. The machine may operate in the capacity of a server or a client machine in a client-server network environment, or as a peer machine in a peer-to-peer (or distributed) network environment. The machine may be a personal computer (PC), a tablet PC a web appliance, a server, cloud computing, or any machine or infrastructure capable of executing a set of instructions (sequential or otherwise) that specify actions to be taken by that machine. The term "machine" shall also be taken to include any collection of machines, computers or products of manufacture that individually or jointly execute a set (or multiple sets) of instructions to perform any one or more of the methodologies of the invention.

In alternative embodiments the computer further comprises a network interface device (adapter). The computer also may include a display device, which can be a video display unit (display device, e.g., a liquid crystal display (LCD) or a cathode ray tube (CRT)). The computer also may include a human-machine interface, which can include, for example, an alphanumeric input device (e.g., a keyboard), a cursor control device (e.g., a mouse), and a signal generation device (e.g., a speaker). In addition to the human-machine interface, the computer may also include an input/output interface.

In alternative embodiments, the data storage device (e.g., drive unit) comprises a computer-readable storage medium on which is stored one or more sets of instructions (e.g., software) embodying any one or more of the protocols, methodologies or functions of this invention. The instructions may also reside, completely or at least partially, within the main memory and/or within the processor during execution thereof by the computer, the main memory and the processor also constituting machine-accessible storage media. The instructions may further be transmitted or received over a network via the network interface device.

In alternative embodiments the computer-readable storage medium is used to store data structure sets that define user identifying states and user preferences that define user profiles. Data structure sets and user profiles may also be stored in other sections of computer system, such as static memory.

In alternative embodiments, while the computer-readable storage medium in an exemplary embodiment is a single medium, the term "machine-accessible storage medium" can be taken to include a single medium or multiple media (e.g., a centralized or distributed database, and/or associated caches and servers) that store the one or more sets of instructions. In alternative embodiments the term "machine-accessible storage medium" can also be taken to include any medium that is capable of storing, encoding or carrying a set of instructions for execution by the machine and that cause the machine to perform any one or more of the methodologies of the present invention. In alternative embodiments the term "machine-accessible storage medium" shall accordingly be taken to include, but not be limited to, solid-state memories, and optical and magnetic media.

In alternative embodiments, information and signals are represented using any technology and/or technique known in the art. For example, data, instructions, commands, information, signals, bits, symbols, and chips used to practice the compositions (devices, computers) and methods of the invention can be represented by voltages, currents, electromagnetic waves, magnetic fields or particles, optical fields or particles, or any combination thereof.

In alternative embodiments, the various illustrative logical blocks, modules, circuits, and algorithm steps used to describe exemplary embodiments can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The algorithms and displays presented herein are not inherently related to any particular computer or other apparatus. Various general-purpose systems may be used with programs in accordance with the teachings herein, or it may prove convenient to construct a more specialized apparatus to perform the method steps. In addition, the present disclosure is not described with reference to any particular programming language. In alternative embodiments, a variety of programming languages are used to implement the embodiments of the invention as described herein.

The embodiments may be used for root analysis of any plant species, including, but not limited to, monocots and dicots. Examples of plants of interest include, but are not limited to, corn (*Zea mays*), *Brassica* sp. (e.g., *B. napus, B. raga, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, *sorghum*, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

In some embodiments, the methods are useful for assessing efficacy of insecticidal materials against certain insects selected from the orders Coleoptera, Diptera, Lepidoptera, Homoptera, and Hemiptera, particularly Coleoptera.

Larvae of the order Lepidoptera include, but are not limited to, cutworms; *Agrotis ipsilon* Hufnagel (black cutworm); *A. orthogonia* Morrison (western cutworm); *A. subterranea* Fabricius (granulate cutworm); *Athetis mindara* Barnes and Mcdunnough (rough skinned cutworm); *Euxoa messoria* Harris (darksided cutworm); *Egira* (Xylomyges) *curialis* Grote (*citrus* cutworm); borers; *Crambus caliginosellus* Clemens (corn root webworm); and *Elasmopalpus lignosellus* Zeller (lesser cornstalk borer).

Of interest are larvae and adults of the order Coleoptera including rootworms and flea beetles in the family Chrysomelidae, including, but not limited to: *Diabrotica virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); and *Colaspis brunnea* Fabricius (grape colaspis).

Adults and immatures of the order Diptera are of interest, including maggots including, but not limited to: *Delia platura* Meigen (seedcorn maggot); and *D. radicum* (cabbage maggot).

Agronomically important members from the order Homoptera further include, but are not limited to: *A. maidiradicis* Forbes (corn root aphid).

Agronomically important species of interest from the order Hemiptera include, but are not limited to: *S. castanea* (root stink bug).

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Methods for measuring the activity of an insecticidal material as a reference point are known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. For purposes of an insecticidal protein, generally the protein is mixed and used in feeding assays. See, for example Marrone, et al., (1985) *J. of Economic Entomology* 78:290-293. Such assays can include contacting a food source with one or more insects and determining the insect's ability to survive.

Although the foregoing embodiments of the invention have been described in some detail by way of illustration and example for clarity of understanding, certain changes and modifications are encompassed within the scope of the appended claims.

The methods will be further understood by reference to the following non-limiting Examples. The following Examples are provided for illustrative purposes only. The Examples are included solely to aid in a more complete understanding of the described embodiments of the invention. The Examples do not limit the scope of the embodiments of the invention described or claimed.

EXAMPLES

Example 1—Manual Corn Rootworm Nodal Injury Scoring Procedure

Whole plant greenhouse bioassays were conducted to screen maize plants for feeding by *D. virgifera*. Plants consisted of a corn inbred with at least one transgene expressing at least one insecticidal protein in roots, or a wild type seed-grown plant of the same genetic background without the transgene to serve as a negative control. Plants were grown in 3.78 L plastic pots, maintained in controlled environment (80-82 F, 16:8 L:D) and watered as needed. At the V2-V3 leaf stage, plants were infested with approximately 400 non-diapausing *D. virgifera virgifera* eggs (two infestations of ~200 eggs one week apart). Plants were scored for *D. virgifera virgifera* feeding 19-21 days after the first infestation. To assign insect feeding scores, plants were removed from the pot and potting media was washed away from the crown and the root given a manual node-injury-score by an evaluator (CRWNIS) (Oleson et al. 2005, Journal of Economic Entomology 98:1, p. 1-8.). Plants may be placed back into their container, repotted and grown for seed production.

Example 2—Automated Corn Rootworm Nodal Injury Scoring Method Using CT

Whole plant greenhouse bioassays were conducted to screen maize plants for feeding by *D. virgifera virgifera*, where the plants were raised and infested in the same manner as set forth in Example 1. To assign insect feeding scores, plants were transported to an X-ray CT scanner, and the pot volume was scanned using a 3D helical scan approach. After scanning, the plants were returned to the growing environment. The CT scanner data was used to reconstruct the 3D pot volume, after which the roots were distinguished (segmented) from the soil using segmentation algorithms to reveal the relevant root structure. After segmentation of the root structure, a quantification method related the observed 3D structure to a usable root nodal injury score. Quantification took the form of manual evaluation and scoring of the segmented image in the manner of Oleson, et. al. Additionally, further analysis and scoring of the segmented data was done automatically via algorithm. In this case additional features measured or extrapolated from the segmented data set, including but not limited to; root volume, length, branching morphology, depth distribution, etc., may be included in the analyses.

Example 3—Correlation of Non-Destructive CT-Derived Nodal Injury Score to Standard Method, and Distinguishing of Transgenic Treatment Effect To compare the method of CT based root damage assessment verses traditionally derived nodal injury scores, CT image datasets were generated for 3 different treatments:

a. Rootworm infested plants with strong positive insect herbivore protectant b. Rootworm infested plants with a moderate positive insect herbivore protectant c. Rootworm infested Wild Type plants with no protection Candidate plants were grown as described above in Example 1 in a controlled growth environment and X-ray imaged to generate 3D volumes for root segmentation. The candidate plants were then destructively harvested, including root washing, for manual scoring of the corn rootworm nodal injury score. After completion of the CT image processing, the segmented 3D image data sets were then visually scored for corn rootworm nodal injury score and compared to the standard manual scores obtained from destructive harvesting.

Figure 1:
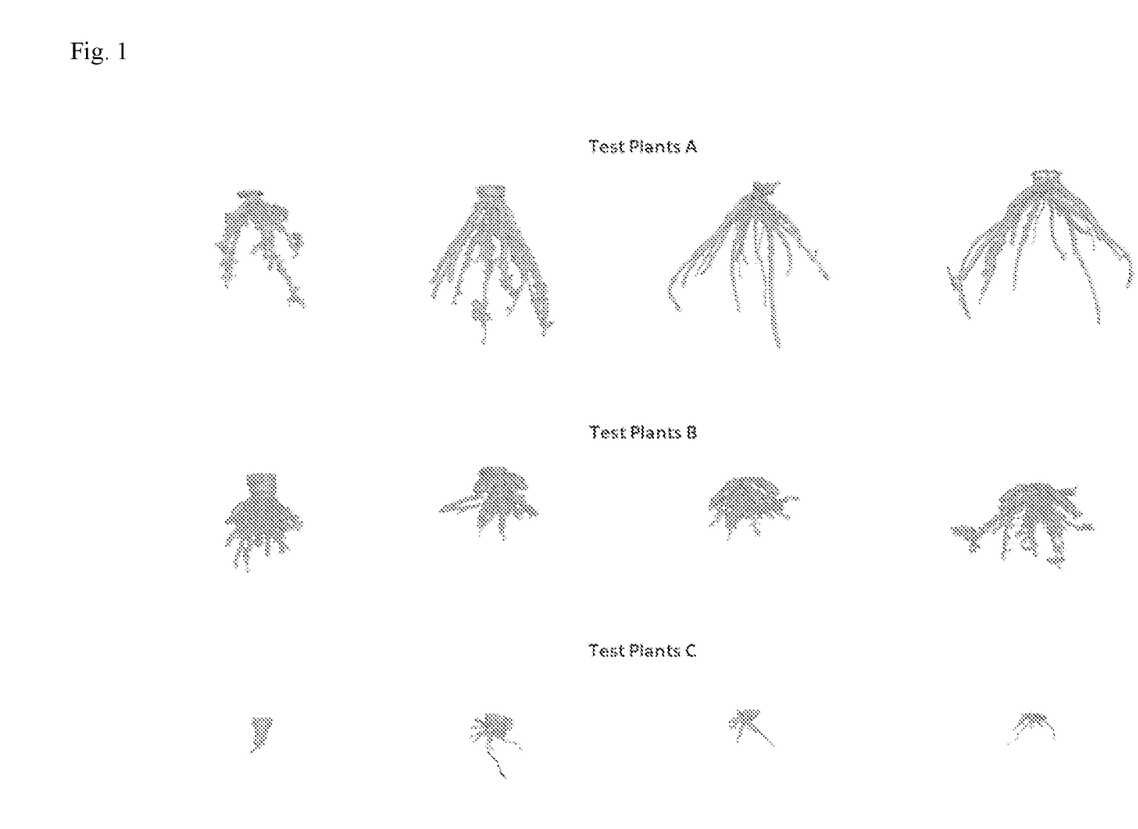
FIG. 1: 3D reconstructions of root structures distinguishing differential treatment effects across genotypes.
Figure 2:
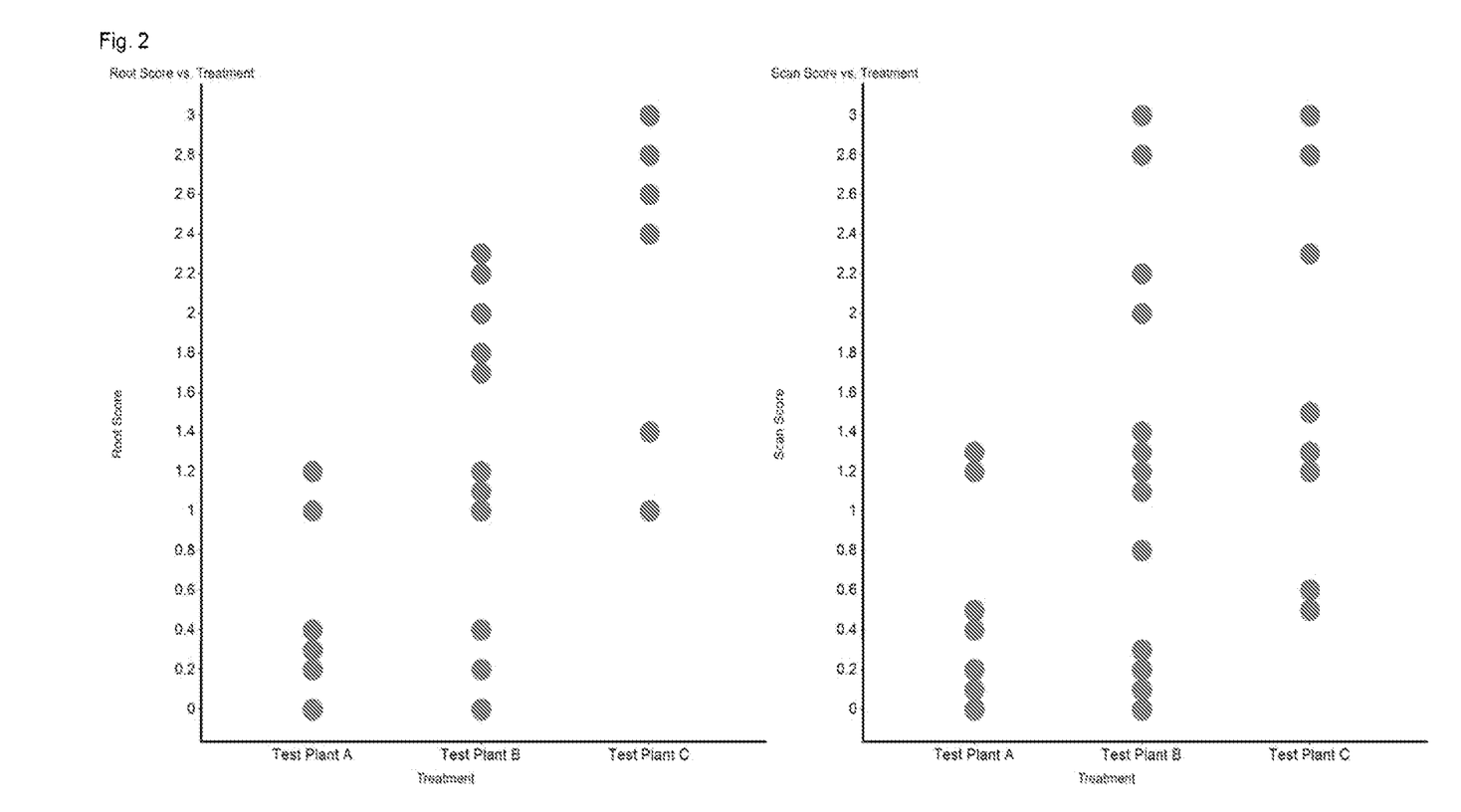
FIG. 2: CT derived corn rootworm nodal injury scores correlated with manually assessed corn rootworm nodal injury scores.

As depicted in FIG. 1, 3D reconstructions of the root structure were of sufficient quality to distinguish differential treatment effect across genotypes. As shown in FIG. 2, CT image derived corn rootworm nodal injury scores correlated well with manually derived, destructively-harvested corn rootworm nodal injury scores.

Results of the CT assessment indicate that the scanning method is capable of sufficiently reconstructing 3D root datasets to reliably allow for an image-derived corn rootworm nodal injury score that correlates well with the manual corn rootworm nodal injury score obtained from destructive harvesting.

Example 4—Time Course Assessment of Root Feeding Progression Via Multiple CT Measurements By conducting multiple CT scans across the course of root pest feeding, it is possible that a more precise assessment of per plant root growth and root damage can be obtained over a given time course. Previous manual assessment may prevent continual evaluation of plant root growth/mass due to both the disruption of the insect lifecycle and the impact on plant health as a result of the invasive scoring procedure. Using the non-destructive methodology disclosed herein, it is possible to track the progression of root damage across time. Additionally, information provided on root mass may offer some indication of whether insecticidal material (applied or transgenic) has an impact on insect root herbivory.

To evaluate multiple measurements of nodal injury score and CT derived root traits, 3 sets of 15 candidate plants each were grown with standard root worm assay as described in International Application Publication Number WO2017/066094, incorporated herein by reference, in a controlled growth environment and X-ray imaged to generate 3D volumes for root segmentation. The candidate plants were also destructively harvested, including root washing, for manual scoring of corn rootworm nodal injury score. However, in this example, the individual sets of candidate plants were non-destructively imaged and destructively scored at the following time points: 1.) at infestation +7 days; 2.) at infestation +14 days; and, 3.) at infestation +21 days.

Figure 3:
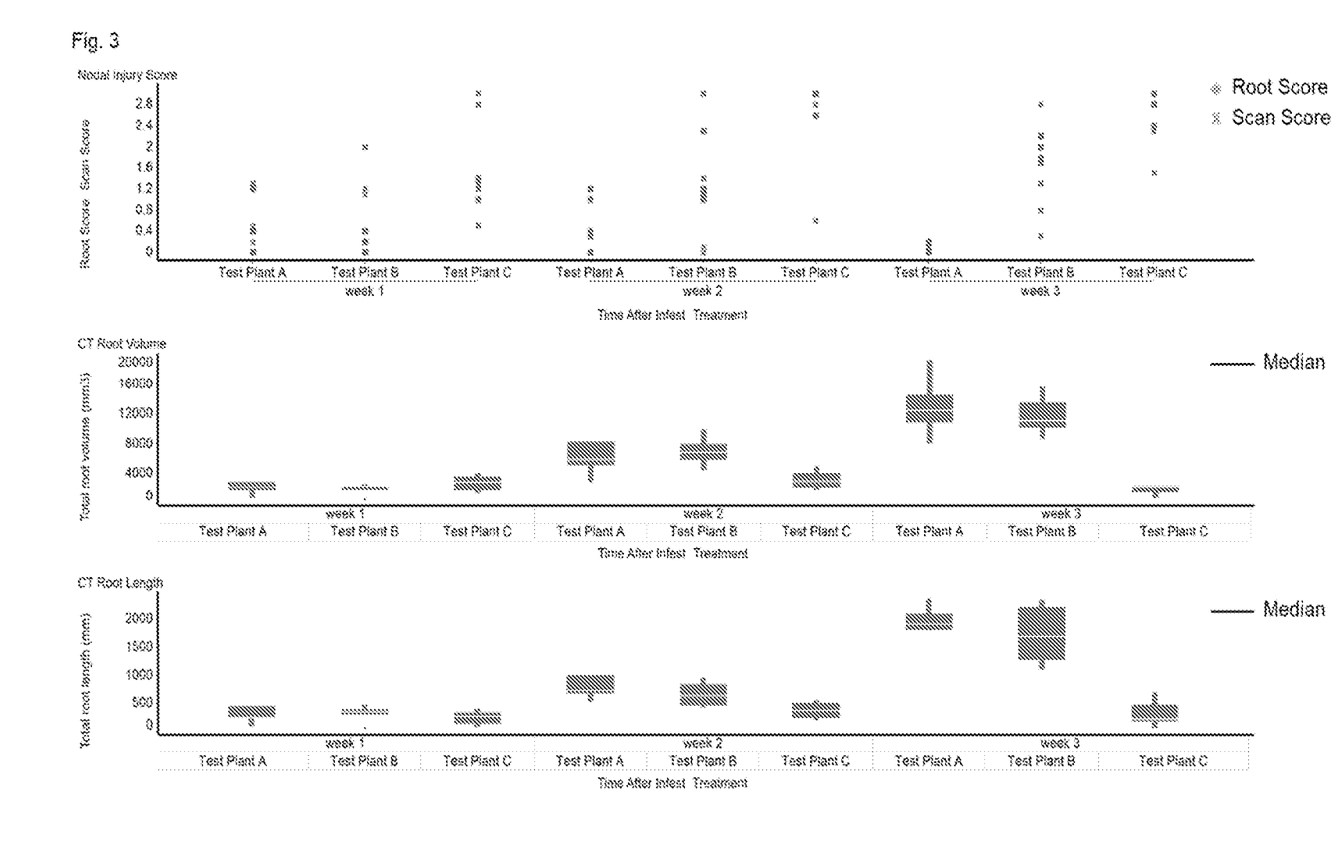
FIG. 3: X-ray CT image data at various time points for the continuous evaluation of root damage.

For all three time points, X-ray CT image datasets were generated for 3 different treatments:

a. Rootworm infested plants with a strong positive insect herbivore protectant b. Rootworm infested plants with a moderate positive insect herbivore protectant c. Rootworm infested Wild Type plants with no protection As shown in FIG. 3, nodal injury scores obtained from the X-ray CT allow for the continuous evaluation of root damage at earlier time points than the previous destructive evaluation methods, indicating that the +14-day time point can produce scores complementary to those obtained at +21 days, whereas the +7-day measurement appears to be too early in both root development and feeding progression and therefore may have a limited value. Additionally, evaluation of X-ray CT derived root volume and length across the time-course provide new insight into root growth rate and feeding progression as relates to the effects of insecticidal material.

Example 5—Evaluation of Candidate Transgenes Using Automated CT Corn Rootworm Nodal Injury Scoring Method Whole plant greenhouse bioassays were conducted to screen maize plants for feeding by *D. virgifera*, where the plants were raised and infested in the same manner as set forth in Examples 1 & 2. To evaluate efficacy of candidate transgenes expressing at least one insecticidal protein in roots, candidate plants were raised, infested, scanned via CT using a 3D helical scan approach, and assigned feeding scores in the same manner as set forth in Example 2. Candidate plants consisted of 33 treatments:

A. Rootworm infested plants with strong positive insect herbivore protectant

B. Rootworm infested Wild Type plants with no protection

C. Rootworm infested inbred plants with at least one transgene expressing at least one insecticidal protein in roots. 31 independent transgene treatments were evaluated.

A total of 218 test plants were evaluated; 20 treatment A positive controls, 40 treatment B negative controls, and 158 treatment C transgenic plants—consisting of 31 independent transgene treatments, each consisting of up to 6 plants.

Plants were non-destructively imaged with a CT scanner and the data was reconstructed and segmented to reveal the root structures as set forth in Example 2. Of the original 218 plants scanned, 36 scans were suppressed due to technical faults in some combination of raw image acquisition, reconstruction, or root segmentation. As previously described, resultant segmented root images were assigned a root nodal injury score, and in this case, each root image was assigned a nodal injury score by two independent evaluators applying the scoring method of Oleson et al. (2005). To cross-validate the CT derived nodal injury scores, each plant was then destructively harvested, including root washing, for manual scoring of the corn rootworm nodal injury score.

Figure 4:
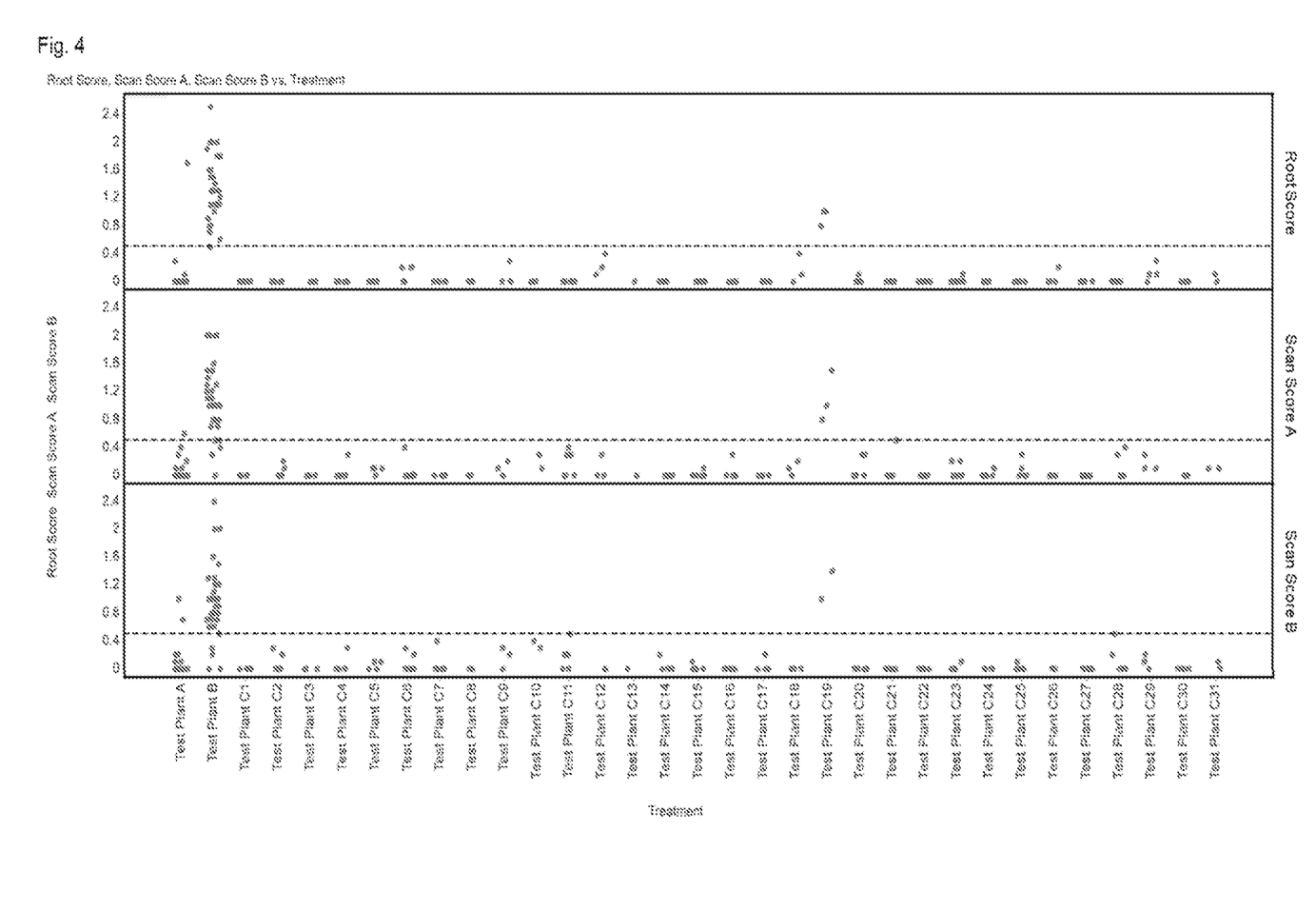
FIG. 4: Comparison of nodal injury scores generated via CT scan and nodal injury score produced via destructive measurement.

As depicted in FIG. 4, nodal injury scores generated via CT data for both independent evaluators show at high level of agreement with the nodal injury score produced via destructive measurement. This is apparent both on an individual plant basis and for the aggregate of each treatment. For purposes of screening treatment efficacy, a "pass/fail" threshold was set at a nodal injury score level of 0.5. By this metric, agreement between the CT derived and destructively derived scores at the treatment level for C1-C31 was 100%.

Figure 5:
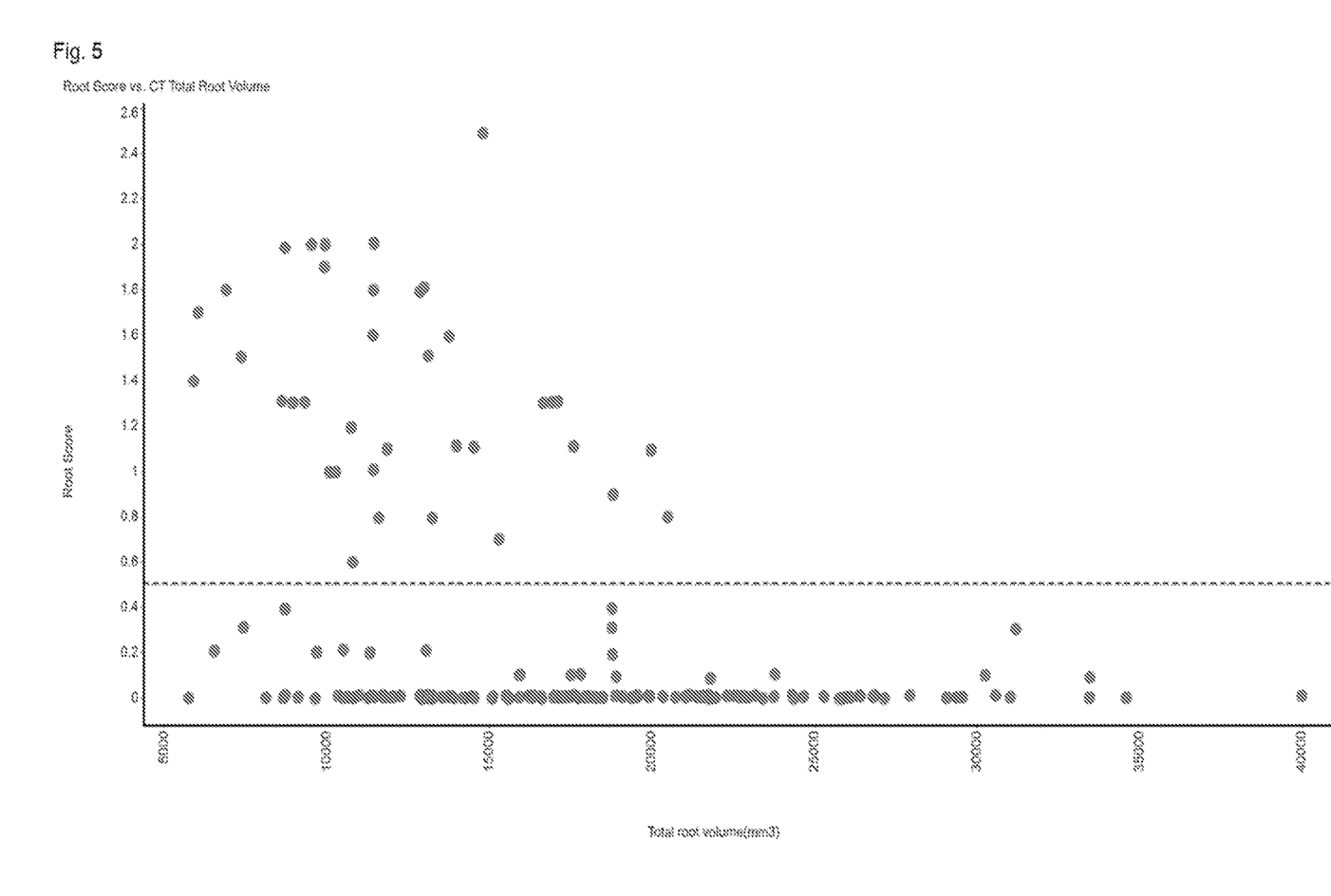
FIG. 5: Comparison of Root Volumetric data and Nodal Injury Score.

Example 6—Augmentation of Nodal Injury Score Screening Method with CT Derived Root Volumetric Data Segmented root image datasets described in Example 5 were further evaluated for correlation of Root Volume to destructively derived nodal injury score. Total root volume was derived from each of the segmented images, as set forth in Example 4. As depicted in FIG. 5, comparison of the CT derived volume to the manual nodal injury score demonstrates relationships that can be used to augment the nodal injury score evaluation, and to potentially streamline the candidate efficacy assay as described in Example 5.

Examination of the CT volume data indicate that all individual plants with volume in excess of 21.00 mm3 fall below the 0.5 nodal injury score threshold set for pass/fail, representing 48 plants, or 26% of plants evaluated via CT. This indicates that volumetric data from the CT image could be used to effectively pre-screen candidate plants; with plants above the indicated volume threshold expected to pass and therefore not needing further evaluation. Additionally, all negative control plants, and the Transgenic treatment that failed the nodal injury score threshold, cluster together, with modest overlap in volume as compared to plants below the nodal injury score pass threshold. This indicates potential value in CT derived volumetric data as potential component of future automated analysis methods.

What is claimed is:

1. A method of non-destructively determining the resistance of candidate plant roots to insect herbivory, comprising:
    (a) subjecting root tissue of the candidate plant to at least one insect root herbivore,
    (b) obtaining a non-destructive image of roots of said candidate plant, wherein the candidate plant roots are substantially embedded in the soil, and determining the resistance of the candidate plant roots to insect herbivory based on injury to the root tissue, and
    (c) growing said candidate plant or another plant for seed production.

2. The method of claim 1, comprising obtaining the non-destructive image using X-ray computed tomography.

3. The method of claim 1, comprising obtaining the root images of at least two candidate plants simultaneously or sequentially.

4. The method of claim 1, wherein the injury to the root tissue results in a determination of a root nodal injury score.

5. The method of claim 1, comprising determining the injury to the root tissue by measuring root volume, root length, root growth rate, root branching morphology, or root depth distribution.

6. The method of claim 5, comprising determining the injury to the root tissue by a processor, the method further comprising manually using the non-destructive image to generate the root nodal injury score.

7. The method of claim 1, comprising generating the root nodal injury score by a processor, wherein said processor receives a digital image and generates a root nodal injury score.

8. The method of claim 1, wherein the insect root herbivore is a *Diabrotica* species.

9. The method of claim 8, wherein said *Diabrotica* species is selected from the group consisting of *Diabrotica virgifera, Diabrotica undecimpunctata howardi*, and *Diabrotica barberi*.

10. A method of non-destructively determining root injury, comprising subjecting root tissue of a candidate plant to at least one insect root herbivore, presenting the candidate plant to a non-destructive imaging apparatus, obtaining a non-destructive image of roots of said candidate plant, and generating a root nodal injury score.

11. The method of claim 1 or claim 10, comprising obtaining additional non-destructive images of roots of said candidate plant at two or more time intervals.

12. The method of claim 11, wherein the two or more images are compared using imaging software.

13. The method of claim 1 or claim 10, wherein the candidate plant is selected from corn, *Brassica* sp., alfalfa, rice, *sorghum*, millet, sunflower, safflower, wheat, soybean, and tobacco.

14. The method of claim 10, comprising presenting the candidate plant to the imaging apparatus in a pot.

15. The method of claim 10, comprising presenting the candidate plant to the imaging apparatus by an automated movement system.

16. The method of claim 15, wherein the automated movement system comprises a transportation belt.

17. The method of claim 10, wherein the imaging apparatus comprises an X-ray imager.

18. The method of claim 10, wherein the non-destructive image is obtained using X-ray computed tomography.

19. The method of claim 10, comprising obtaining the root images of at least two candidate plants simultaneously or sequentially.

20. The method of claim 10, comprising manually generating the root nodal injury score using the non-destructive image.

21. The method of claim 10, comprising generating the root nodal injury score by a processor, wherein said processor receives a digital image and generates a root nodal injury score.

22. The method of claim 10, wherein the insect root herbivore is a *Diabrotica* species.

23. The method of claim 22, wherein said *Diabrotica* species is selected from the group consisting of *Diabrotica virgifera, Diabrotica undecimpunctata howardi*, and *Diabrotica barberi*.

* * * * *